United States Patent [19]

Lu

[11] Patent Number: 4,690,948
[45] Date of Patent: Sep. 1, 1987

[54] HALOGENATED RESORCYLIC ACID LACTONE DERIVATIVES

[75] Inventor: Jing-Jong Lu, Terre Haute, Ind.

[73] Assignee: International Minerals & Chemical Corp., Terre Haute, Ind.

[21] Appl. No.: 936,715

[22] Filed: Dec. 1, 1986

[51] Int. Cl.$^4$ ............................................. C07C 65/01
[52] U.S. Cl. .................................. 514/544; 514/568; 549/427; 549/428; 560/55; 560/65; 560/75; 562/465; 562/478; 568/630; 568/634; 568/649; 568/655; 568/663; 568/765; 568/774; 570/182
[58] Field of Search ............... 514/544, 568; 549/427, 549/428; 560/55, 65, 75; 562/465, 478; 568/630, 634, 649, 658, 663, 765, 774; 570/182

[56] References Cited

U.S. PATENT DOCUMENTS

| | | | |
|---|---|---|---|
| 3,196,019 | 7/1965 | Andrews et al. | 99/2 |
| 3,239,341 | 3/1966 | Hodge et al. | 99/2 |
| 3,239,345 | 3/1966 | Hodge et al. | 99/2 |
| 3,239,346 | 3/1966 | Hodge et al. | 99/2 |
| 3,239,348 | 3/1966 | Hodge et al. | 99/2 |
| 3,239,354 | 3/1966 | Hodge et al. | 99/2 |
| 3,562,313 | 2/1971 | Cross et al. | 260/473 |
| 3,660,562 | 5/1972 | Grass et al. | 424/279 |
| 3,687,982 | 8/1972 | Young | 260/343.2 |
| 3,860,616 | 1/1975 | Hoffsommer et al. | 260/343.2 |
| 4,035,504 | 7/1977 | Hidy et al. | 424/279 |
| 4,088,658 | 5/1978 | Robertson | 260/343.41 |
| 4,225,593 | 9/1980 | Davies et al. | 260/345.8 |
| 4,409,392 | 10/1983 | Hodge | 260/343.41 |
| 4,443,470 | 4/1984 | Hodge et al. | 424/279 |

FOREIGN PATENT DOCUMENTS 1194911 7/1970 United Kingdom .

OTHER PUBLICATIONS

Hidy et al., "Zearalenone and Some Derivatives: Production and Biological Activities", Adv. Appl. Microbiol., 22:59–82 (1977).
Chalupa, "Manipulating Rumen Fermentation", J. Am. Sci., vol. 46, No. 3, p. 585 (1977).
Shipchandler, "Chemistry of Zearalanone and Some of Its Derivatives", Heterocycles, 3(6): 471–520 (1975).
Peters et al., "A Stereoselective Synthetic Route to (R)-Zearalanone", J. Med. Chem., vol. 18, No. 2, 215-217 (1975).
Kuo et al., "The Resolution of Zearalenone. Determination of the Absolute Configuration of the Natural Enantiomorph", Chemical Communications, p. 761 (1967).

Primary Examiner—Paul J. Killos
Attorney, Agent, or Firm—Wendell R. Guffey; Thomas L. Farquer

[57] ABSTRACT

Ring opened halogenated Resorcyclic Acid Lactone (RAL) derivatives having the structure:

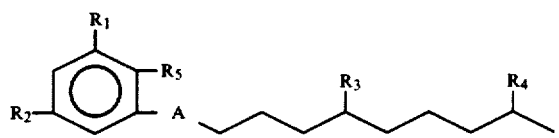

are used to increase rumen fermentation efficiency.

20 Claims, No Drawings

HALOGENATED RESORCYLIC ACID LACTONE DERIVATIVES

This invention relates generally to Resorcylic Acid Lactone (RAL) derivatives and particularly to ring opened halogenated RAL derivatives useful for increasing rumen fermentation effiency.

BACKGROUND OF THE INVENTION

Zearalenone and its derivatives are the basic RAL compounds used as the starting materials for the compounds of the present invention. Zearalenone has the following structural formula:

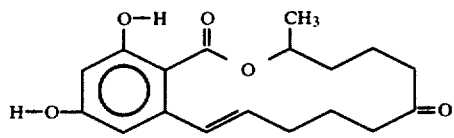

Zearalenone may be prepared by culturing the zearalenone producing strain of *Gibberella zeae* as taught in U.S. Pat. No. 3,196,019, incorporated herein by reference. Zearalenone and its ring-opened and other derivatives have been reviewed in the literature. Shipchandler, *Heterocycles*, 3(6):471-520 (1975) and Hidy et al "Zearalenone and Some Derivatives: Production and Biological Activities", *Adv. Appl. Microbiol.*, 22:59-82 (1977).

Zearalenone has been chemically modified to form numerous derivatives. U.S. Pat. No. 3,239,348, incorporated herein by reference, discloses a method for producing zearalenol from zearalenone by reducing the ketone carbonyl group. U.S. Pat. No. 3,239,345, incorporated herein by reference, discloses a method for producing zearalanol from zearalenone and zearalenol by reducing the ketone carbonyl group and/or the macrocylic ring double bond. Zearalenol has the following structural formula:

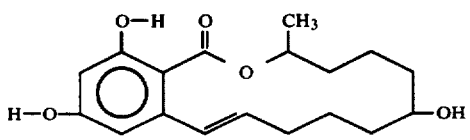

Zearalanol has the following structural formula:

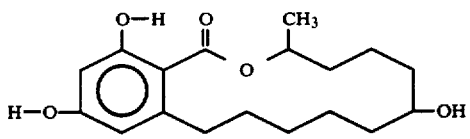

U.S. Pat. No. 3,239,341, incorporated herein by reference, discloses a method for producing zearalene by reduction of the ketone carbonyl group following by dehydration reactions and zearalane by subsequently hydrogenating the double bond in the presence of a palladium catalyst. U.S. Pat. No. 3,239,349 discloses a method for producing iodine derivatives of zearalenone. U.S. Pat. Nos. 3,239,343 and 3,239,344 disclose a method for producing RAL nitrogen derivatives by replacing the ketone carbonyl group. U.S. Pat. No. 4,088,658 discloses a method for producing dideoxyzearalane by removing the two phenolic hydroxyl groups. U.S. Pat. No. 3,687,982 discloses a method for separating mixed diastereoisomers of Zearalanol. U.S. Pat. No. 3,997,568 discloses a method for converting (10'S)-Zearalenone to (10'R)-Zearalenone.

These compounds have generally been used as antimicrobial agents to fight infections, anti-inflammatory agents to reduce or lessen swelling. These compounds, however, have often been difficult to administer or have undesirable side effects, and have not been as highly effective for the intended purpose as desirable. There is, therefore, a continuing need for new compounds that can reduce problems with administration, lessen the toxic and other undesirable side effects, and improve upon the efficacy of such compounds.

Methods for increasing rumen fermentation efficiency are known in the art: U.S. Pat. No. 4,225,593 to Davies et al. discloses the use of aplasmomycin, boromycin and acylated and hydrogenated derivatives thereof for modifying rumen metabolism in domestic ruminant animals by reducing the proportion of methane formed and increasing the proportion of propionate at the expense of methane and/or acetate. U.S. Pat. No. 3,660,562 discloses compositions and methods for improving feed efficiency in ruminants by inhibiting methanogenesis in the rumen utilizing halogenated hydrocarbons such as chloroform, carbon tetrachloride, methylene chloride, and hexachloroethane. These compounds and methods, however, are not highly efficient, may be somewhat toxic to the animal, and are often difficult to use. There exists, therefore, a continuing need for new compounds and methods for increasing rumen fermentation efficiency.

SUMMARY OF THE INVENTION

It is, therefore, an object of the present invention to provide a method for increasing rumen fermentation efficiency in ruminants.

It is another object of the present invention to provide halogenated RAL derivatives useful for increasing rumen fermentation efficiency.

It is another object of the present invention to provide a feed composition containing halogenated RAL derivatives which is useful for increasing rumen fermentation efficiency.

These and other objects are achieved by synthesizing halogenated RAL derivatives which increase rumen fermentation effiencicy having the structure:

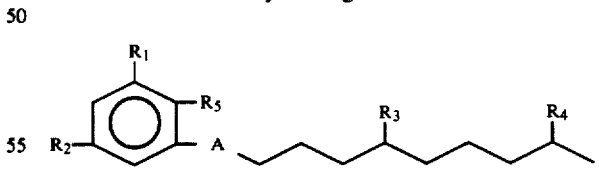

wherein A is $CH_2-CH_2$ or $CH=CH$; $R_1$ and $R_2$, which may be the same or different, are H, OH, $OCH_3$, OBz, oxytetrahydropyran (OTHP) or OZ, where Z is an alkyl group having from 2-6 carbon atoms; $R_3$ is a halogen or OH; $R_4$ is a halogen; and $R_5$ is H, $CO_2H$, or $CO_2Z$, where Z is $CH_3$, $CH_2OCH_3$, $CH_2SCH_3$, or tetrahydropyran (THP).

Preferably, A is $CH_2-CH_2$ or $CH=CH$; $R_1$ and $R_2$ are H, $R_1$ and $R_2$ are OH, $R_1$ is OH and $R_2$ is H, $R_1$ is H and $R_2$ is OH, $R_1$ is $OCH_3$ and $R_2$ is OH, $R_1$ and $R_2$ are OBz, $R_1$ is H and $R_2$ is OBz, $R_1$ and $R_2$ are OTHP, or $R_1$ or OH and $R_2$ is OTHP; $R_3$ is Br, Cl, or OH; $R_4$ is Br or Cl; and $R_5$ is H or $CO_2H$.

The RAL derivatives of the present invention are administered to ruminants to increase rumen fermentation efficiency. The RAL derivatives reduce the amount of animal feed that is converted to methane gas, decrease the acetate to proponate ratio in the ruminant, and increase the amount of metabolic hydrogen recovered in the metabolic process. This improvement in rumen fermentation efficiency increases feed utilization efficiency by making more dietary energy available to the animal and, therefore, improves the animal's growth performance for the amount of food consumed.

Other objects, advantages, and novel features of the present invention will become apparent from the following detailed description of the invention.

DETAILED DESCRIPTION OF THE INVENTION

In accordance with the present invention, a compound is synthesized having the formula:

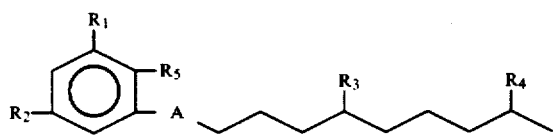

wherein A is $CH_2$—$CH_2$ or $CH=CH$; $R_1$ and $R_2$, which may be the same or different, are H, OH, $OCH_3$, OBz, oxytetrahydropyran (OTHP) or OZ, where Z is an alkyl group having from 2-6 carbon atoms; $R_3$ is a halogen or OH; $R_4$ is a halogen; and $R_5$ is H, $CO_2H$, or $CO_2Z$, where Z is $CH_3$, $CH_2OCH_3$, $CH_2SCH_3$, or tetrahydropyran (THP) is synthesized and used to increase rumen fermentation effeciency in ruminants.

Preferably, A is $CH_2$—$CH_2$ or $CH=CH$; $R_1$ and $R_2$ are H, $R_1$ and $R_2$ are OH, $R_1$ is OH and $R_2$ is H, $R_1$ is H and $R_2$ is OH, $R_1$ is $OCH_3$ and $R_2$ is OH, $R_1$ and $R_2$ are OBz, $R_1$ is H and $R_2$ is OBz, $R_1$ and $R_2$ are OTHP, or $R_1$ is OH and $R_2$ is OTHP; $R_3$ is Br, Cl, or OH; $R_4$ is Br or Cl; and $R_5$ is H or $CO_2H$.

Most preferably, $R_1$ and $R_2$ are OH or $OCH_3$, A is $CH=CH$, $R_5$ is H or $CO_2H$, $R_3$ is Br, Cl, or OH; and $R_4$ is Br or Cl.

The compounds of the present invention are synthesized according to the general scheme shown in FIG. 1. Alkyl groups were added to the phenolic hydroxyl groups by means well known to those skilled in the art. The lactone ring is cleaved by reacting the alkylated compound with a strong base such as aqueous sodium hydroxide (NaOH) to give a series of known ring-open compounds. These ring-opened compounds were converted to the halogenated compounds of the present invention by reacting with an appropriate halogenating agent using methods disclosed hereinafter.

Alkyl groups are added to the phenolic hydroxyl groups to produce $R_1$ and $R_2$ by means well known to those skilled in the art. U.S. Pat. Nos. 3,239,341, 3,239,346, 3,239,348, and 3,239,354, incorporated herein by reference, disclose several methods for producing esters at the $R_1$ and the $R_2$ positions of the present compound.

The lactone ring is opened by reacting the RAL compound with a strong base such as aqueous sodium hydroxide (NaOH) in an appropriate solvent such as DMSO to produce a series of ring-open RAL compounds by means well known to those skilled in the art.

C. A. Peters and R. N. Hurd; *J. Med. Chem.*, 18(2):215 (1971) and C. H. Kao and W. H. Urry et al., *Chemical Communications;* 761 (1967) disclose the methods for producing ring-open RAL derivatives. M. T. Shipchandler, *Heterocycles,* 3(6):11, table 11, (1975) discloses a series of ring-open RAL compounds. U.S. Pat. No. 3,562,313, incorporated herein by reference, and British Pat. No. 1,193,911 disclose the process of independent synthesis of this series of ring-open RAL compounds. These compounds are used as starting materials or intermediates in the present invention.

These known ring-open RAL compounds are converted to the halogenated compounds of the present invention by reacting an appropriate halogenating agent with the hydroxyl groups on the ring-opened section of the molecule. Generally, an excess of halogenating agent in an appropriate solvent is reacted with the ring-open RAL compound to produce the compounds of the present invention. Heating the reaction mixture to moderate temperatures will speed the reaction. Heating the reactants to 75° C. in HOAc has been shown to produce the present halogenated compounds quickly and efficiently.

Most halogenating agents can be used to react with the ring-opened compounds to produce the halogenated compounds of the present invention. $SO_2Cl_2$, $SOCl_2$, $PCl_5$, $SO_2Br_2$, hydrobromic acid, and boron tribromide, are typical examples. Molecular halogen compounds such as $Br_2$ and $Cl_2$, however, cannot be used to halogenate compounds having the macrocyclic ring double bond because the halogenating agent will also react with the double bond and/or benzene ring. Generally, when A is $CH=CH$, halogenating agents such as hydrobromic acid, boron tribromide or thionyl chloride are preferred.

The RAL derivatives of the present invention are administered to ruminants to increase rumen fermentation efficiency. The RAL derivatives reduce the amount of animal feed that is converted to methane gas, decrease the acetate to proponate ratio in the ruminant, and increase the amount of metabolic hydrogen recovered in the metabolic process. This improvement in rumen ferementation efficiency increases feed utilization efficiency by making more dietary energy available to the animal and, therefore, improves the animal's growth performance for the amount of food consumed.

The compounds of the present invention can be administered to ruminants by any suitable method, preferably oral administration. For example, the compounds of the present invention can be blended with ordinary feed compositions in amounts sufficient to increase fermentation efficiency and can thus be fed directly to the ruminants. The compounds of the present invention can also be administered in the animal's drinking water, given as tablets, suspensions, syrups, solutions, and the like.

When the compounds of the present are to be administered in feeds, an animal feed composition may be prepared containing the usual nutritionally-balanced animal feed having the required quantities of carbohydrates, proteins, vitamins and minerals, together with one or more halogenated RAL compounds in accordance with the present invention. Some of the usual dietary elements included in animal feed compositions are grains, such as ground grain and grain byproducts, animal protein substances, such as those found in fish meal and meat scraps, vegetable proteins, like soybean oil meal or peanut oil meal; vitamins and vitamin-containing materials, e.g., vitamin A and D mixtures, riboflavin supplements and other vitamin B complex members; and bone meal and limestone to provide minerals. A type of conventional feed material for use with cattle includes alfalfa hay and ground corncobs together with supplementary vitamins and vitamin-containing substances if desired.

It is preferable that the compounds of the present invention be administered to ruminants in amounts sufficient to be present in the ruminants rumenal fluid at concentrations of from about 5 ppm to about 1000 ppm, more preferably from about 50 ppm to about 500 ppm. These amounts can conveniently be achieved by mixing the compounds of the present invention with the animal's feed composition in an amount from about 5–1100 grams per ton of feed, preferably from about 50–550 grams per ton of feed.

The invention having been generally described, the following examples are given as particular embodiments of the invention and to demonstrate the practice and advantages thereof. U.S. Pat. Nos. 3,196,019, 3,239,341, 3,239,342, 3,239,343, 3,239,344, 3,239,345, 3,239,346, 3,239,347, 3,239,348, 3,239,349, 3,239,350, 3,239,351, 3,239,352, 3,239,353, and 3,239,354, incorporated herein by reference, disclose methods for producing Zearalenone, Zearalanone, Zearalene, Zearalane, Zearalenol, Zearalanol, and various esters and other derivatives of these compounds. These compounds and their derivatives, particularly the ester derivatives, can be halogenated by the methods in the present invention. It is understood that the examples are given by way of illustration and are not intended to limit the specification or the claims to follow in any manner. In particular, the specification and claims as written are intended to include all isomers of the compounds and the alkyl groups are intended to include linear and branched chains. The examples include some isomer structure for illustrative purposes only. To simplify the chemical structures, H atoms are generally not shown.

EXPERIMENTAL EXAMPLES

The ring opened halogenated resorcylic acid lactone derivatives useful for increasing rumen fermentation efficiency may be prepared as follows:

EXAMPLE 1

The Preparation of 2,4-Dimethyl Derivative of 6'(S)-Zearalenol

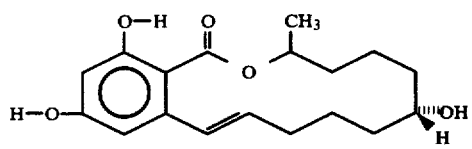

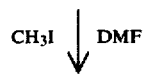

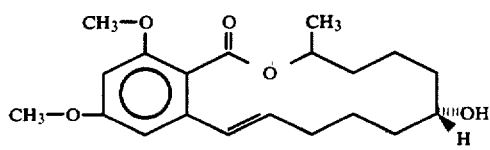

To a mixture of 6'(S)-zearalenol (32.0 g, 0.1 mol) and anhydrous potassium carbonate ($K_2CO_3$) (55.3 g, 0.4 mole) in 300 ml of dimethylformamide (DMF) was added slowly 59.3 g (0.42 mole) of iodomethane ($CH_3I$). The reaction mixture was stirred at room temperature for 5 hours and poured into water, extracted with chloroform. The chloroform solution was washed with water, dried over anhydrous $MgSO_4$ and concentrated to remove $CHCl_3$ and DMF. The residue was purified by flash chromatography on silica gel eluted with 3:1, 1:1 petroleum ether/ethyl acetate, ethyl acetate to give 30.7 g of 2,4-dimethyl derivative of 6'(S)-zearalenol, PMR($\delta$) (CDCl$_3$) 1.32 (d, 3H), 1.20–2.00 (m, 10H), 2.00–2.45 (m, 2H), 3.40 (m, 1H), 3.77 (s, 3H), 3.78 (s, 3H), 5.35 (m, 1H), 6.1 (m, 1H), 6.30 (d, 1H), 6.58 (d, 1H), 8.65 (d, 1H), and 1.03 g of 2,4-dimethyl-6'-formyl derivative of 6'(S)-zearalenol, PMR($\delta$) (CDCl$_3$) 1.34 (d, 3H), 1.35–1.90 (m, 10H), 2.31 (m, 2H), 3,81 (s, 3H), 3.84 (s, 3H), 5.38 (m, 1H), 6.15 (m, 1H), 6.38 (s, 1H), 6.61 (m, 1H), 8.07 (s, 1H).

EXAMPLE 2

The Preparation of 2,4-Dimethyl Derivative of 6'(R)-Zearalenol

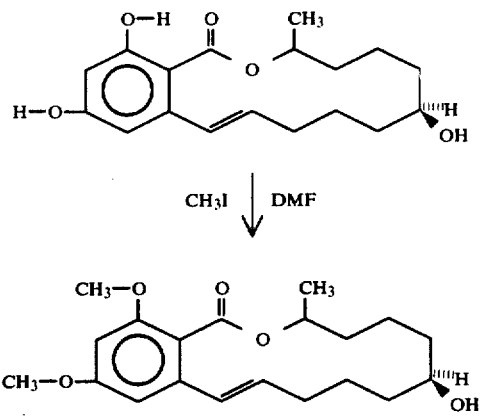

To a mixture of 6'(R)-zearalenol (16.0 g, 0.050 mol) and anhydrous $K_2CO_3$ (27.7 g, 0.2 mol) in 150 ml of dimethylformamide was added slowly 28.7 g (0.2 mol) of iodomethane. The reaction mixture was stirred at room temperature for 5 hours. The resulting solution was poured into water, then extracted with chloroform. The chloroform solution was washed with water, dried over anhydrous $MgSO_4$, and concentrated in an evaporator. The residue was purified by flash chromatography on silica gel eluted with 3:1, 1:1 petroleum ether/ethyl acetate to give 15.6 of 2,4-dimethyl derivative of 6'(R)-zearalenol; PMR($\delta$) (CDCl$_3$) 1.38 (d, 3H), 1.35–1.95 (m, 10H), 2.70 (m, 2H), 3.77 (s, 3H), 3.81 (s, 3H), 5.20 (m, 1H), 6.00–6.73 (m, 4H), and 1.0 g of 4-methyl derivative of 6'(R)-zearalenol. PMR($\delta$) (CDCl$_3$) 1.38 (d, 3H), 1.30–2.00 (m, 10H), 2.00–2.53 (m, 2H), 3.81 (s, 3H), 5.00 (m, 1H), 5.80 (m, 1H), 6.46 (m, 2H), 7.10 (d, 2H), 12.23 (s, 1H).

EXAMPLE 3

The Preparation of
2,4-Dimethyoxy-6-[6'(S),10'(S)dihydroxy-trans-1-undecenyl]benzoic Acid

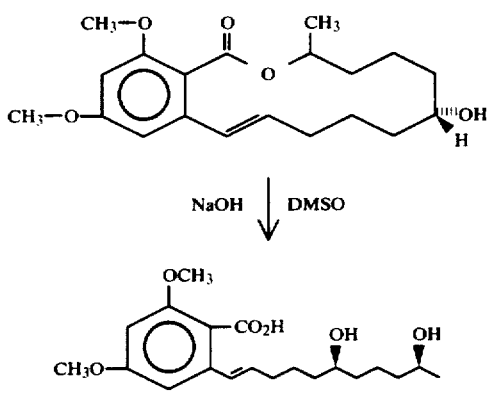

To a solution of 2,4-dimethoxy-6-[6'(S),10'(S)-dihydroxy-trans-1-undecenyl]benzoic acid μ-lactone (6.96 g, 20 mmol) in 150 ml of dimethyl sulfoxide (DMSO) was added 17 ml of 40% NaOH solution and the reaction solution was heated at 120° C. for 5 hours under $N_2$. The resulting solution was cooled, poured into ice water, acidified with 10% $H_2SO_4$ solution and then extracted with $CHCl_3$. The $CHCl_3$ solution was washed with water, dried over anhydrous $Na_2SO_4$ and concentrated to give 5.66 g of residue. The residue was purified by flash chromatography on silica gel eluted with ethyl acetate; 10:1, 5:1, 3:1 ethyl acetate/methanol to give 3.70 g of 2,4-dimethoxy-6-[6'(S),10'(S)-dihydroxy-trans-1-undecenyl]benzoic acid. PMR(δ) (CDCl₃) 1.00–2.00 (m, 15H), 2.88 (m, 2H), 3.50 (m, 9H), 3.81 (s, 6H), 5.42 (m, 2H), 6.35 (s, 2H).

EXAMPLE 4

The Preparation of
2,4-Dimethoxy-6-[6'-[6'(R),10'(S)-dihydroxy-trans-1-undecenyl]benzoic Acid

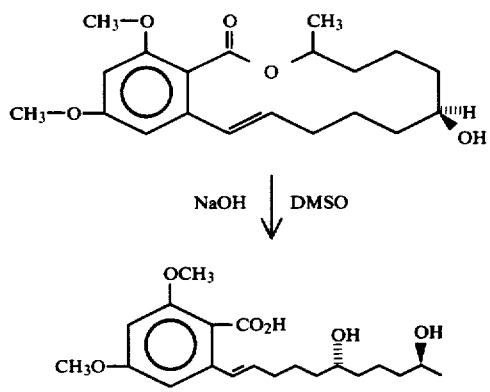

To a solution of 2,4-dimethoxy-6-[6'(R),10'(S)-dihydroxy-trans-1-undecenyl]benzoic acid μ-lactone (6.96 g, 20 mmol) in 150 ml of DMSO was added 17 ml of 40% NaOH solution and the reaction solution was heated at 120° C. for 5 hours. The resulting solution was cooled, poured into ice water, acidified with 10% $H_2SO_4$ solution and extracted with chloroform. The chloroform solution was washed with water, dried over anhydrous $Na_2SO_4$ and concentrated to give 6.59 g of residue. The residue was purified by flash chromatography on silica gel eluted with ethyl acetate, 10:1, 5:1, 3:1 ethyl acetate/methanol to give 4.58 g of 2,4-dimethoxy-6'[6'(R),10'(S)-dihydroxy-trans-1-undecenyl]benzoic acid. PMR(δ) (CDCl₃) 1.09 (d, 3H), 1.09–2.10 (m, 12H), 2.86 (m, 2H), 3.62 (m, 2H), 3.88 (s, 6H), 4.92 (m, 2H), 6.38 (s, 2H).

EXAMPLE 5

The Preparation of
2-Hydroxy-4-methoxy-6'[6',10'-dibromo-trans-1-undecenyl]benzoic Acid

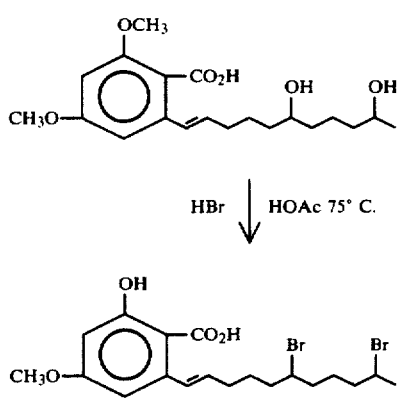

The solution of 1.0 g of 2,4-dimethoxy-6'[6'(S),10'(S)-dihydroxy-trans-1-undecenyl]benzoic acid and 30 ml of hydrobromic acid (30 wt % solution to acetic acid) mixture was heated at 75° C. for 30 min. The resulting solution was added to sodium bicarbonate solution at 0° C. and the product was extracted with ethyl ether. The ethyl ether solution was dried over anhydrous $MgSO_4$ and concentrated in an evaporator. The residue was purified by flash chromatography on silica gel eluted with 3:1, 1:1 petroleum ether/ethyl aceate to give 0.67 g of the product; PMR(δ) (CDCl₃) 1.30–2.35 (m, 15H), 3.81 (s, 3H), 4.08 (m, 2H), 6.31 (m, 2H), 11.20 (s, 1H), MS (EI) m/e (rel. intensity) 478 (M+, 38.1), 446 (35.2), 339 (53.5), 397 (54.8), 299 (26.9), 193 (100), 165 (73.6), 164 (73.8), 137 (55.9); Calc. for $C_{19}H_{26}O_4Br_2$, C 47.72%, H 5.48% Found C 47.78%, H 5.73%.

EXAMPLE 6

The Preparation of
2-Methoxy-4-hydroxy-6'[6'(S)-hydroxy-10'-bromo-trans-1-undecenyl]benzoic Acid and
2-Methoxy-4-hydroxy-6-[6'(S),10'(S)-dihydroxy-trans-1-undecenyl]benzoic Acid

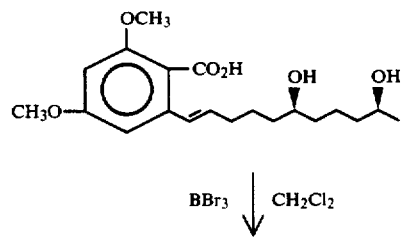

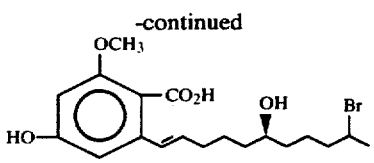

To a solution of 760 mg of 2,4-dimethoxy-6-[6'(S),10'(S)-dihydroxy-trans-1-undecenyl]benzoic acid in 35 ml of $CH_2Cl_2$ at $-78°$ C. was added dropwise 8.0 ml of 1.0M of $BBr_3$ in $CH_2Cl_2$ under nitrogen. The reaction solution was stirred at $-78°$ C. for 2 hours, then quenched with distilled water. The resulting solution was poured into 200 ml of water and then extracted with ethyl ether. The ethyl ether solution was dried over anhydrous $MgSO_4$, then concentrated in an evaporator. The residue was purified by flash chromatography on silica gel eluted with 1:1 petroleum ether/ethyl acetate, ethyl acetate, 10:1 ethyl acetate/methanol to give 310 mg of 2-methoxy-4-hydroxy-6-[6'(S)-hydroxy-10-bromo-trans-1-undecenyl]benzoic acid. PMR($\delta$) ($CDCl_3$) 1.00–2.50 (m, 13H), 3.85 (s, 3H), 6.31 (m, 2H), 7.28 (s, 1H), 8.10 (m, 1H), MS (CI) m/e (rel. intensity) 417 ($M^{30}+3$, 45.4), 415 ($M^+ +1$, 47.1), 399 (51.4), 397 (46.8), 373 (24.8), 371 (26.4), 335 ($M^+ +1$—HBr, 100), 319 (20.0), 317 (25.2), 291 ($M^+ +1$—$CO_2$—HBr, 70.1) and 280 mg of 2-methoxy-4-hydroxy-6-[6'(S),10'(S)-dihydroxy-trans-1-undecenyl]-benzoic acid; PMR($\delta$) ($CDCl_3$) 0.75–2.00 (m, 13H), 3.73 (s, 3H), 6.23 (m, 2H), 7.27 (s, 1H), 8.11 (m, 1H), MS (CI) m/e (rel. intensity) 335 ($M^+ +1$—$H_2O$, 5.6), 319 (12.5), 309 (50.4), 292 (19.3), 291 ($M^+ +1$—$CO_2$—$H_2O$, 100).

EXAMPLE 7

The Preparation of 2-Methoxy-4-hydroxy-6-[6'(R)-hydroxy-10'-bromo-trans-1-undecenyl]benzoic Acid and 2-Methoxy-4-hydroxy-6-[6'(R),10'(S)-dihydroxy-trans-1-undecenyl]benzoic Acid

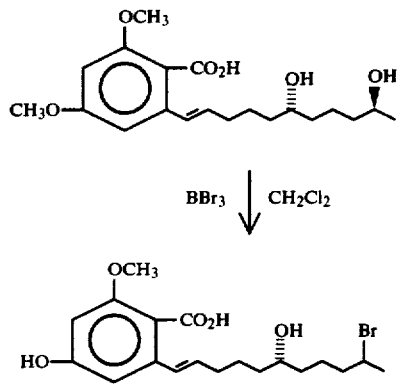

To a solution of 800 mg of 2,4-dimethoxy-6-[6'(R),10'(S)-dihydroxy-trans-1-undecenyl]benzoic acid in 40 ml of $CH_2Cl_2$ at $-78°$ C. was added dropwise 8.0 ml of 1.0M of $BBr_3$ in $CH_2Cl_2$ under nitrogen. The reaction solution was stirred at $-78°$ C. for 2 hours, then quenched with distilled water. The resulting solution was poured into 200 ml of water, and then extracted with ethyl ether. The ethyl ether solution was dried over anhydrous $MgSO_4$, and then concentrated in an evaporator. The residue was purified by flash chromatography on silica gel eluted with 1:1 petroleum ether/ethyl acetate, ethyl acetate, 10:1 ethyl acetate/methanol to give 340 mg of 2-methoxy-4-hydroxy-6-[6'(R)-hydroxy-10'-bromo-trans-1-undecenyl]benzoic acid; PMR($\delta$) ($CDCl_3$) 1.00–2.00 (m, 10H), 1.62 (d 3H), 2.58–3.58 (m, 3H), 3,81 (s, 3H), 4.00 (m, 1H), 6.31 (d, 2H), 7.30 (s, 1H), MS (CI) m/e (rel. intensity) 417 ($M^+ +3$,4.2), 415 ($M^+ +1$, 4.7), 399 (10.5), 397 (5.4) 373 (27.0), 371 ($M^+ +1$—$CO_2$, 29.2), 335 ($M^+ +1$—HBr, 23.6) 292 (20.5 ), 291 ($M^+ +1$—$CO_2$—HBr, 100) and 330 mg of 2-methoxy-4-hydroxy-6-[6'(R), 10'(S)-dihydroxy-trans-1-undecenyl]benzoic acid; PMR($\delta$) ($CDCl_3$) 0.75–1.90 (m, 13H), 2.50–3.80 (m, 3H), 6.23 (m, 2H), 727 (s, 1H); MS (CI) m/e (rel. intensity) 335 ($M^+ +1$—$H_2O$, 7.7), 319 (15.1), 309 (38.5), 292 (20.5), 291 ($M^+ +1$—$CO_2$—$H_2O$, 100).

IN VITRO RUMEN FLUID TEST

The ability of halogenated recorcylic acid lactone derivatives of the present invention to inhibit methane synthesis and enhance production of desirable volatile fatty acids (VFA) was demonstrated by an in vitro test system described as follows: Rumen fluid was obtained from a fistulated steer maintained on a hay diet containing a mineral supplement. Fluid was removed from the rumen, strained through four layers of cheese cloth under a stream of carbon dioxide, and transported into an anaerobic chamber containing an atmosphere of 97% carbon dioxide and 3% hydrogen. All subsequent operations were carried out under anaerobic conditions inside the chamber. The strained rumen fluid was diluted with an equal volume of anaerobic McDougall's buffer. Fourteen mils of diluted rumen fluid was added to 60 ml Wheaton serum bottles containing 70 mg of finely ground hay. Vials were sealed with butyl rubber stoppers, secured with aluminum crip caps, transported from the chamber, and headspace gas was exchanged with 100% carbon dioxide. Addition of test compounds was carried out by injection. Test compounds were added in 0.5 ml methanol, untreated controls received 0.5 methanol without additive. Vials were incubated 16 hrs. at 39° C. on a rotary shaker (100 rpm). Following incubation, headspace samples were analyzed for methane for gas chromatography. Incubated rumen fluid was clarified by centrifugation, and analyzed for volatile fatty acids by gas chromatography. The results are summarized in Table 1.

Referring to Table 1, the compounds tested were labeled as follows: 2-Methoxy-4-hydroxy-6-[6'(R)-hydroxy-10'-bromo-trans-1-undecenyl]benzoic Acid (Compound 1), 2-Methoxy-4-hydroxy-6'[6'(S)-hydroxy-10'-bromo-trans-1-undecenyl]Benzoic Acid (Compound 2), and 2-Hydroxy-4-methoxy-6[6',10'-dibromo-trans-1-undecenyl]benzoic Acid (Compound 3). Fermentation efficiency was calculated as described by Chalupa, J. Anim. Sci. 46: 585: Fermentation efficiency=(0.62 moles acetate+1.09 moles propionate+0.78 moles butyrate)÷(moles acetate+moles propionate+moles butyrate)×100. Results indicate that the compounds of the present invention inhibit formation of methane gas, a desirable effect. The reduction in methane is accompanied by a decrease in the acetate to propionate ratio thus increasing the useful energy recovered from the feed. This alteration in volatile fatty acid (VFA) production improves rumen fermentation efficiency by increasing the amount of metabolic hydrogen recovered. The improvement in fermentation efficiency makes more dietary energy available to the animal, less is lost through production of methane gas, and hence animal's growth performance is improved for the amount of food consumed.

Obviously many modifications and variations of the present invention are possible in light of the above teachings. It is, therefore, to be understood that within the scope of the appended claims the invention may be practiced otherwise than as specifically described.

TABLE 1

Effect of Halogenated Resorcylic Acid Lactone Net Values on in vitro Rumen Fermentation

| Compound (500 ppm) | Acetate μm/ml | Propionate μm/ml | Butyrate μm/ml |
|---|---|---|---|
| Control | | | |
| Mean | 57.79 | 14.87 | 9.91 |
| Std Dev | 7.16 | 2.01 | 1.49 |
| 1 | | | |
| Mean | 43.18 | 17.87 | 8.89 |
| Std Dev | 8.70 | 1.30 | 1.39 |
| 2 | | | |
| Mean | 22.85 | 20.42 | 2.95 |
| Std Dev | 3.79 | 2.34 | 1.69 |
| 3 | | | |
| Mean | 34.15 | 18.98 | 16.99 |
| Std Dev | 2.01 | 1.81 | 1.98 |

| Compound (500 ppm) | Acetate/ Propionate | Total VFA | Fermentation Efficiency | Percent $CH_4$ |
|---|---|---|---|---|
| Control | | | | |
| Mean | 3.89 | 82.58 | 72.37 | 7.11 |
| Std Dev | 0.05 | 10.67 | 0.11 | 0.40 |
| 1 | | | | |
| Mean | 2.40 | 69.94 | 76.16 | 2.94 |
| Std Dev | 0.34 | 11.12 | 1.18 | 0.06 |
| 2 | | | | |
| Mean | 1.15 | 45.23 | 83.87 | 0.65 |
| Std Dev | 0.87 | 6.97 | 1.06 | 0.64 |
| 3 | | | | |
| Mean | 1.80 | 70.13 | 78.58 | 0.05 |
| Std Dev | 0.07 | 5.75 | 0.31 | 0.00 |

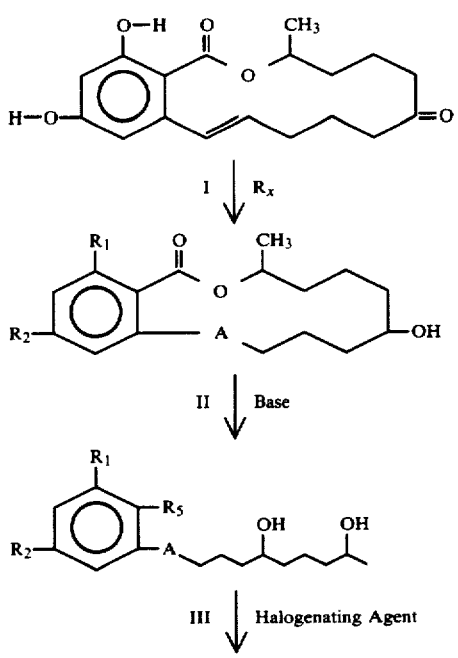

Figure 1

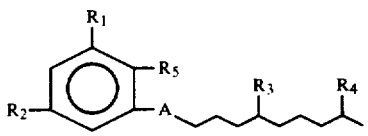

IV

I claim:

1. A compound having the formula

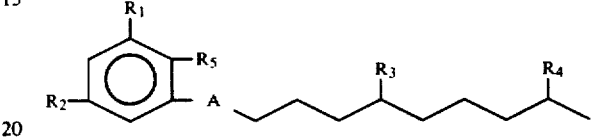

wherein A is $CH_2-CH_2$ or $CH=CH$; $R_1$ and $R_2$, which may be the same or different, are H, OH, $OCH_3$, OBz, OTHP, or OZ, where Z is an alkyl group having from 2-6 carbon atoms; $R_3$ is a halogen or OH; $R_4$ is a halogen; and $R_5$ is H, $CO_2H$, or $CO_2Z$, where Z is $CH_3$, $CH_2OCH_3$, $CH_2SCH_3$, or THP.

2. The compound of claim 1 wherein A is $CH_2-CH_2$ or $CH=CH$; $R_1$ and $R_2$ are H, $R_1$ and $R_2$ are OH, $R_1$ is OH and $R_2$ is H, $R_1$ is H and $R_2$ is OH, $R_1$ is $OCH_3$ and $R_2$ is OH, $R_1$ and $R_2$ are OBz, $R_1$ is H and $R_2$ is OBz, $R_1$ and $R_2$ are OTHP, or $R_1$ is OH and $R_2$ is OTHP; $R_3$ is Br, Cl, or OH; $R_4$ is Br or Cl; and $R_5$ is H, $CO_2H$, or $CO_2Z$, where Z is $CH_3$, $CH_2OCH_3$, $CH_2SCH_3$, or tetrahydropyran (THP).

3. The compound of claim 1 wherein $R_1$ and $R_2$ are OH or $OCH_3$, A is $CH=CH$ or $CH_2-CH_2$, $R_5$ is H or $CO_2H$, $R_3$ is Br, Cl, or OH; and $R_4$ is Br or Cl.

4. The compound of claim 1 wherein $R_1$ is $OCH_3$; $R_2$ is OH; $R_5$ is H; A is $CH=CH$; $R_3$ is OH; and $R_4$ is Br.

5. The compound of claim 1 wherein $R_1$ is $OCH_3$; $R_2$ is OH; $R_5$ is $CO_2H$; A is $CH=CH$; $R_3$ is OH; and $R_4$ is Br.

6. The compound of claim 1 wherein $R_1$ is $OCH_3$; $R_2$ is OH; $R_5$ is H; A is $CH=CH$; $R_3$ is Br; and $R_4$ is Br.

7. A method for increasing rumen fermentation efficiency in ruminants comprising the step of orally administering to said ruminants a rumen fermentation efficiency increasing amount of a compound having the formula:

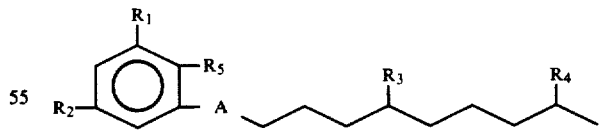

wherein A is $CH_2-CH_2$ or $CH=CH$; $R_1$ and $R_2$, which may be the same or different, are H, OH, $OCH_3$, OBz, OTHP, or OZ, where Z is an alkyl group having from 2-6 carbon atoms; $R_3$ is a halogen or OH; $R_4$ is a halogen; and $R_5$ is H, $CO_2H$, or $CO_2Z$, where Z is $CH_3$, $CH_2OCH_3$, $CH_2SCH_3$, or THP.

8. The method of claim 7 wherein A is $CH_2-CH_2$ or $CH=CH$; $R_1$ and $R_2$ are OH, $R_1$ is OH and $R_2$ is H, $R_1$ is H and $R_2$ is OH, $R_1$ is $OCH_3$ and $R_2$ is OH, $R_1$ and $R_2$ are OBz, $R_1$ is H and $R_2$ is OBz, $R_1$ and $R_2$ are OTHP, or $R_1$ or OH and $R_2$ is OTHP; $R_3$ is Br, Cl, or OH; $R_4$ is Br or Cl; and $R_5$ is H, $CO_2H$, or $CO_2Z$, where Z is $CH_3$, $CH_2OCH_3$, $CH_2SCH_3$, or tetrahydropyran (THP).

9. The method of claim 7 wherein $R_1$ and $R_2$ are OH or $OCH_3$, A is CH=CH or $CH_2$—$CH_2$, $R_5$ is H or $CO_2H$, $R_3$ is Br, Cl, or OH; and $R_4$ is Br or Cl.

10. The method of claim 7 wherein $R_1$ is $OCH_3$; $R_2$ is OH; $R_5$ is H; A is CH=CH; $R_3$ is OH; and $R_4$ is Br.

11. The method of claim 7 wherein $R_1$ is $OCH_3$; $R_2$ is OH; $R_5$ is $CO_2H$; A is CH=CH; $R_3$ is OH; and $R_4$ is Br.

12. The method of claim 7 wherein $R_1$ is $OCH_3$; $R_2$ is OH; $R_5$ is H; A is CH=CH; $R_3$ is Br; and $R_4$ is Br.

13. The method of claim 7 wherein said compound is administered to said animal in amounts sufficient to be present in said animal's rumenal fluid at concentrations from about 5 ppm to about 1000 ppm.

14. A feed composition useful as a rumen fermentation modifier comprising a nutritionally-balanced animal feed and a rumen fermentation increasing amount of a compound having the formula:

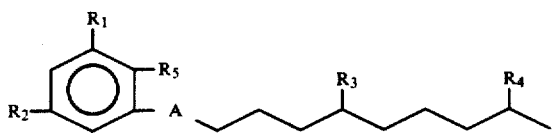

wherein A is $CH_2$—$CH_2$ or CH=CH; $R_1$ and $R_2$, which may be the same or different, are H, OH, $OCH_3$, OBz, THP, or OTHP, or OZ, where Z is an alkyl group having from 2-6 carbon atoms; $R_3$ is a halogen or OH; $R_4$ is a halogen; and $R_5$ is H, $CO_2H$, or $CO_2Z$, where Z is $CH_3$, $CH_2OCH_3$, $CH_2SCH_3$, or THP.

15. The feed composition of claim 14 wherein A is $CH_2$—$CH_2$ or CH=CH; $R_1$ and $R_2$ are H, $R_1$ and $R_2$ are OH, $R_1$ is OH and $R_2$ is H, $R_1$ is H and $R_2$ is OH, $R_1$ is $OCH_3$ and $R_2$ is OH, $R_1$ and $R_2$ are OBz, $R_1$ is H and $R_2$ is OBz, $R_1$ and $R_2$ are OTHP, or $R_1$ is OH and $R_2$ is OTHP; $R_3$ is Br, Cl, or OH; $R_4$ is Br or Cl; and $R_5$ is H, $CO_2H$, or $CO_2Z$, where Z is $CH_3$, $CH_2OCH_3$, $CH_2SCH_3$, or tetrahydropyran (THP).

16. The feed composition of claim 14 wherein $R_1$ and $R_2$ are OH or $OCH_3$, A is CH=CH or $CH_2$—$CH_2$, $R_5$ is H or $CO_2H$, $R_3$ is Br, Cl, or OH; and $R_4$ is Br or Cl.

17. The feed composition of claim 14 wherein $R_1$ is $OCH_3$; $R_2$ is OH; $R_5$ is H; A is CH=CH; $R_3$ is OH; and $R_4$ is Br.

18. The feed composition of claim 14 wherein $R_1$ is $OCH_3$; $R_2$ is OH; $R_5$ is $CO_2H$; A is CH=CH; $R_3$ is OH; and $R_4$ is Br.

19. The feed composition of claim 14 wherein $R_1$ is $OCH_3$; $R_2$ is OH; $R_5$ is H; A is CH=CH; $R_3$ is Br; and $R_4$ is Br.

20. The feed composition of claim 14 wherein said compound comprises from about 5-1100 grams per ton of feed.

* * * * *

UNITED STATES PATENT AND TRADEMARK OFFICE
CERTIFICATE OF CORRECTION

PATENT NO. : 4,690,948

DATED : September 1, 1987

INVENTOR(S) : Jing-Jong Lu

It is certified that error appears in the above-identified patent and that said Letters Patent are hereby corrected as shown below:

Column 1, line 59, "following" should read -- followed --

Column 2, line 49, "effiencicy" should read -- efficiency --

Column 3, line 1, "or" first occurrence, should read -- is --

Column 3, line 7, "proponate" should read -- propionate --

Column 3, line 36, "effeciency" should read -- efficiency --

Column 4, line 41, "proponate" should read -- propionate --

Column 4, line 44, "ferementation" should read -- fermentation --

Column 7, Example 4, in the Heading "The Preparation of 2,4-Dimethoxy-6[6'-[6'(R), 10'(S)-dihydroxy-trans-1-undecenyl]benzoic Acid" should read -- The Preparation of 2,4-Dimethoxy-6-[6'(R), 10' (S)-dihydroxy-trans-1-undecenyl]benzoic Acid --

Column 8, line 35, "to" should read -- in --

Column 8, line 42, "aceate" should read -- acetate --

Column 8, line 47, "339" should read -- 399 --

Column 9, line 24, "($M^{30}$ + 3" should read -- ($M^{+}$ + 3 --

Column 10, line 11, Following "(m, 3H)," insert -- 3.73 (s, 3H), --

Column 10, line 18, "recorcylic" should read -- resorcylic --

Column 10, line 33, "70" should read -- 700 --

UNITED STATES PATENT AND TRADEMARK OFFICE
CERTIFICATE OF CORRECTION

PATENT NO. : 4,690,948

DATED : September 1, 1987

INVENTOR(S) : Jing-Jong Lu

It is certified that error appears in the above-identified patent and that said Letters Patent is hereby corrected as shown below:

Column 10, line 43, "for" should read -- by --

Claim 8, line 5, "or" second occurrence, should read -- is --.

Signed and Sealed this

Twenty-eighth Day of June, 1988

Attest:

DONALD J. QUIGG

*Attesting Officer*  *Commissioner of Patents and Trademarks*